United States Patent
Sinai

(10) Patent No.: US 6,832,708 B2
(45) Date of Patent: Dec. 21, 2004

(54) GLOVE DONNING SYSTEM

(75) Inventor: Dan Sinai, Haifa (IL)

(73) Assignee: Soldon Systems (D.M.S.) Ltd., Hefer (IL)

( * ) Notice: Subject to any disclaimer, the term of this patent is extended or adjusted under 35 U.S.C. 154(b) by 155 days.

(21) Appl. No.: 10/273,510

(22) Filed: Oct. 18, 2002

(65) Prior Publication Data

US 2003/0094468 A1 May 22, 2003

Related U.S. Application Data

(63) Continuation of application No. PCT/IL01/00449, filed on May 20, 2001.

(30) Foreign Application Priority Data

May 25, 2000 (IL) .................................................. 136378

(51) Int. Cl.[7] .............................................. A47G 25/80
(52) U.S. Cl. ..................................................... 223/111
(58) Field of Search .............................. 223/111, 80, 78

(56) References Cited

U.S. PATENT DOCUMENTS

| | | | | |
|---|---|---|---|---|
| 882,312 A | * | 3/1908 | Hoefftcke | .................... 223/111 |
| 3,067,001 A | | 12/1962 | McCollum | |
| 3,323,846 A | * | 6/1967 | Boddy | ............................ 312/1 |
| 3,695,493 A | * | 10/1972 | Karr | ............................ 223/111 |
| 3,715,065 A | * | 2/1973 | Peck | ............................ 223/111 |
| 4,002,276 A | * | 1/1977 | Poncy et al. | .................. 223/111 |
| 4,069,913 A | | 1/1978 | Harrigan | |
| 4,155,494 A | | 5/1979 | Poncy et al. | |
| 4,228,935 A | | 10/1980 | Madray | |
| 4,275,812 A | | 6/1981 | Poncy et al. | |
| 4,889,266 A | * | 12/1989 | Wight | ........................ 223/111 |
| 4,898,309 A | | 2/1990 | Fischer | |
| 4,915,272 A | * | 4/1990 | Vlock | ......................... 223/111 |
| 5,058,785 A | * | 10/1991 | Rich et al. | .................... 223/111 |
| 5,078,308 A | * | 1/1992 | Sullivan | ....................... 223/111 |
| 5,456,354 A | * | 10/1995 | Wood | ........................... 206/278 |
| 5,584,390 A | * | 12/1996 | Wood | ........................... 206/278 |
| 5,590,764 A | * | 1/1997 | Wood | ........................... 206/278 |
| 5,593,071 A | * | 1/1997 | Lusk | ............................ 223/112 |
| 5,769,289 A | * | 6/1998 | Lusk | ............................ 223/112 |
| 6,053,380 A | * | 4/2000 | Sherrod | ........................ 223/111 |
| 6,419,131 B1 | * | 7/2002 | Rix | ................................ 223/111 |
| 6,435,388 B1 | * | 8/2002 | Binder et al. | ................ 223/111 |

FOREIGN PATENT DOCUMENTS

| | | |
|---|---|---|
| DE | 200354 | 12/1907 |
| GB | 943757 | 12/1963 |
| WO | WO 93/04637 | 3/1993 |

* cited by examiner

Primary Examiner—John J. Calvert
Assistant Examiner—James G Smith
(74) Attorney, Agent, or Firm—Frommer Lawrence & Haug LLP; William S. Frommer

(57) ABSTRACT

A glove donning system and method, the arrangement having typically a vacuum wand for grasping the outer skin of the cuff portion of a glove, after which the wand together with the glove is suitably transported to a vacuum chamber, where the cuff portion is aligned with the rim of the opening of the vacuum chamber. By grasping only the outer skin of the glove, the cuff portion is gently opened sufficiently to enable a deflated inflatable ring to be inserted into the cuff portion. The ring is then inflated while positioned inside the cuff portion, which is thereby expanded until it touches the rim of the vacuum chamber. The rim is provided with a suction ring capable of generating sufficient suction to keep the cuff of the glove pressed against the rim, at which point the inflatable ring may be deflated and removed. A vacuum may then be applied to the chamber, inflating the glove and thus enabling a hand to be inserted thereinto. A donning device may be fitted with a pair of such systems, one for each hand, and further provided with suitable means for stacking and delivering on demand one glove to each vacuum chamber.

39 Claims, 11 Drawing Sheets

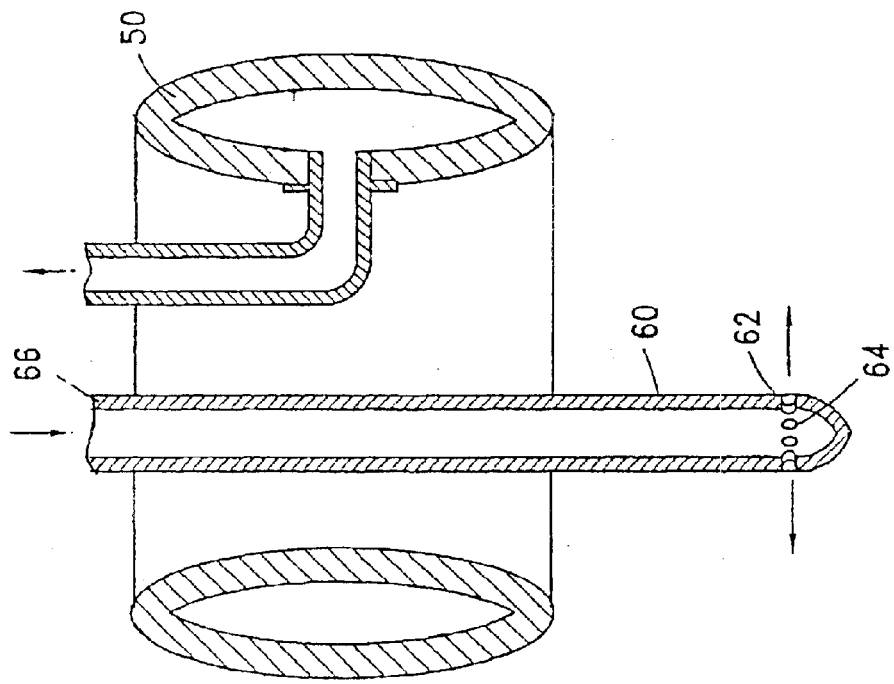
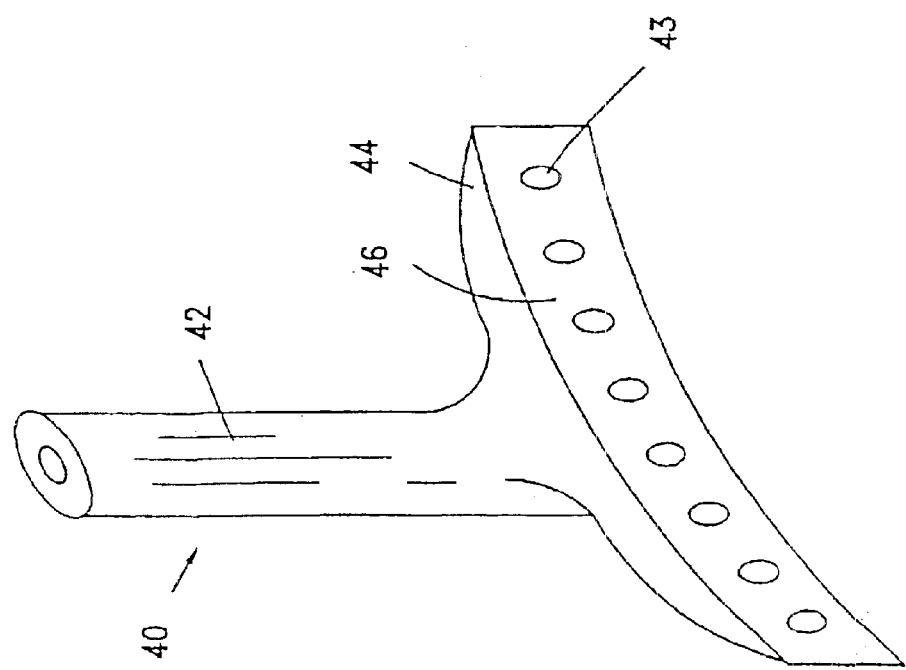
Fig. 5
Fig. 3

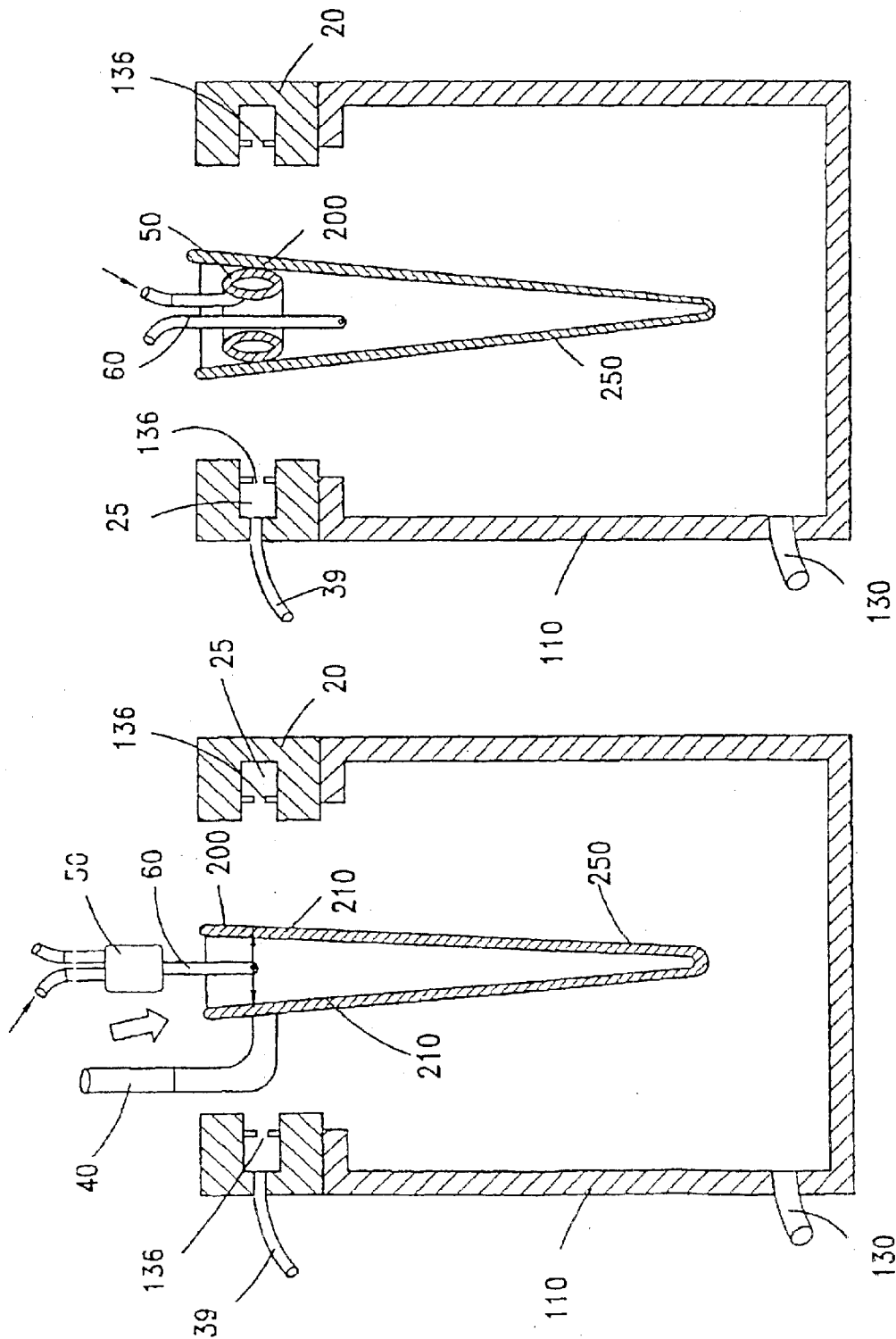

GLOVE DONNING SYSTEM

This is a continuation of copending international application PCT/IL01/00449 having an international filing date of May 20, 2001.

FIELD OF THE INVENTION

The present invention relates primarily to a system and method for facilitating the donning of gloves in an automatic manner such that the user or wearer is not required to manually grasp the gloves during the donning operation. Such a system is of particular use for donning surgical gloves and for donning gloves used in clean rooms in the semiconductor/microprocessor and pharmaceutical industries where avoidance of contamination of gloves is of the highest priority.

BACKGROUND OF THE INVENTION

The importance of donning surgical gloves or gloves used in semiconductor "clean rooms" in a contamination-free manner is well known. The presence of microbial contaminants on the gloves, arising from manual manipulation of the gloves during donning, for example, can have adverse and even lethal effects on a patient undertaking surgery. Similarly, particulate contaminants passed on from a glove can destroy a semiconductor wafer.

Surgeon's and patient examination gloves are intended to provide an effective barrier against potentially infectious materials and other contaminants. However, the use of such gloves has been associated with a number of adverse health effects in patients and users, including allergic reactions, foreign body reactions and irritation. Natural rubber latex (NRL), from which such gloves are generally made, comprises a variety of naturally occurring substances, including plant proteins, which are believed to be the primary allergens associated with natural latex allergy. Nonetheless, NRL gloves provide users with great sensitivity and no suitable synthetic replacement is currently available. However, NRL gloves are difficult to don and doff, and thus glove powder, which comprises cornstarch as a main component thereof, is often used for lubricating the inside surfaces of the gloves. Natural latex allergens are known to bind to cornstarch, and thus the use of donning powder may be pose an additional hazard for allergic personnel and patients. Over the past 3 years, FDA has received requests to ban the use of all glove powders, due to the indications that cornstarch on surgical gloves can reduce tissue resistance to infection, enhance the development of infection and act as a carrier of natural latex protein from NRL products, among others [Federal Register: Jul. 30, 1999 (Volume 64, Number 146) Proposed Rules, Page 41709–41743 from the Federal Register Online via GPO Access (wais.access.gpo.gov), 21 CFR Parts 801, 878, and 880]. In June 1997, the National Institute of Occupational Safety and Health (NIOSH) of the US issued a safety alert recommending the use of powder-free, reduced protein content or synthetic gloves as a means to reduce exposure to natural latex allergens, specifically via the airborne route of exposure [Department of Health and Human Services (NIOSH), "National Institute of Occupational Safety and Health (NIOSH) Alert: Preventing Allergic Reactions to Natural Rubber Latex in the Workplace", Publ. No. 97–135, June 1997.]. While the FDA agrees with the goal of reducing exposure to airborne allergens, it is at the same time concerned that efforts to produce powder-free gloves with satisfactory donning properties may require additional manufacturing processes that, if not appropriately controlled, have deleterious effects on physical properties, performance and shelf-life of the gloves [Aziz, N., "Chlorination of Gloves" Paper No. 5. of the Latex Protein Workshop of the International Rubber Technology Conference, June 1993, Kuala Lumpur, Malaysia; FDA, CDRH, "Environmental Degradation of Latex Gloves: The Effects of Elevated Temperature on Tensile Strength", Division of Mechanics and Materials Science Report # 96-05, D. Walsh, D. Chwirut, R. Kotz, and J. Dawson, Rockville, Md., 1997]. In fact, the FDA is encouraging industry to find a balance between donning requirements—hitherto met by use of the powder—and reducing the risk of adverse health effects.

Rather than using donning powder, lubrication of the gloves may be provided, instead, by a coating or by chlorination. Various kinds of coating are in use. Their manufacture, like the chlorination process, must be carefully controlled to assure a good bond between the coating and the glove. Since the coatings may have different physical properties from that of the NRL glove, they may not generally have the same stretching characteristics, and thus provide a different "feel" to a user than regular NRL gloves.

Chlorination is widely used for reducing the tackiness of natural latex gloves and thus eliminates the need for donning powder. Chlorination works by degrading the surface of the gloves, and thus the chlorination process must be very carefully controlled to prevent destruction of the glove barrier. Improperly chlorinated gloves rapidly degrade, and breaks in the latex film may occur within a span of a few months.

Another concern is the presence of minute defects in the gloves known as pinholes, which directly affect the barrier integrity of the gloves. Studies show that particles such as dust, dirt and other debris may cause pinholes. Furthermore, the glove manufacturing process may also introduce pinholes due to factors such as former vibration, air bubbles in the dripping tanks, dirty formers, incorrect formulation, excessive curing temperatures, and so on. While manufacturers are supposed to comply to minimum manufacturing standards, and while randomised checks are performed, it is still possible for some gloves not meeting the minimum pinhole criteria to be used, leading to the possibility of viruses penetrating the glove, eliminating or reducing the glove's effectiveness as a barrier.

An alternative approach to using less effective synthetic gloves, or to providing NRL gloves with less or alternative forms of lubrication to donning powder, is to provide a glove donning system that reduces the need, and preferably does away with the need entirely, for lubrication. Such a donning system would thus enable regular NRL gloves (as well as any similar type of glove) to be donned without lubrication, in particular donning powder, by elastically deforming the inside of the glove to a volume greater than the hand of the user. In particular, such a system requires the cuff of the glove to be elastically expanded to a size such as to facilitate insertion of a hand therethrough and into the body of the glove.

Automatic glove donning devices are known. Typically, a glove to be donned is held in a vacuum chamber such that the cuff section of the glove is open providing communication between the inside of the glove and the environment of the wearer. The outer surface of the glove is exposed to the vacuum chamber, and thus remains substantially uncontaminated by the wearer environment. When a vacuum is applied to the vacuum chamber, the glove expands within the vacuum chamber by virtue of the greater ambient pressure in the wearer environment, sufficiently to permit a user to insert his hand into the extended glove relatively effortlessly, after which the glove is removed from the vacuum chamber donned on the wearer's hand. Many devices are equipped to don the right-hand and the left-hand gloves from separate dispensers.

These prior art devices, however, comprise inadequate systems for holding the glove within the vacuum chamber in the first place, such as to form an airtight seal between the cuff section of the glove and the chamber. For example, in U.S. Pat. No. 3,695,493, the donning device may only be used with gloves having a cuff portion comprising a special ring made from a rigid material. While the ring permits the glove to sealingly abut against the opening of the vacuum chamber, the device cannot be used with standard gloves, resulting in relatively high running costs for the device. Further, the rigid ring causes difficulties in sealing the cuff portion of the glove onto the wearer's arm.

In U.S. Pat. No. 4,002,276 and U.S. Pat. No. 4,275,812, the gloves come prepared with the cuff portion stretched over a special dedicated ring. Thus, the device cannot be used with standard gloves adding considerably to the running costs of the device since the unit costs of each glove is considerably higher than for standard gloves. Similarly, U.S. Pat. No. 4,069,913 provides a sterilised glove package unit comprising a glove having its cuff portion stretched over a rigid ring, and sealed in an outer protective bag. U.S. Pat. No. 4,155,494 describes a relatively large diameter annular ring onto which the cuff portion of a glove is stretched over prior to donning. U.S. Pat. No. 5,058,785 requires a relatively large stiffening ring for the glove in order to subject the glove to a vacuum. In U.S. Pat. No. 5,078,308 and U.S. Pat. No. 4,915,272, the cuff portion of an elastic glove must be manually stretched over the opening of a cylindrical vacuum tube before it can be donned. In U.S. Pat. No. 4,889,266, a stacked arrangement of glove cartridges enables cartridges to be transported to the opening of a left-hand and of a right-hand vacuum chambers, each cartridge comprising a polygonal glove holder having an opening into which an elastic glove is received, the cuff portion of which is stretched over a lip.

Some glove donning systems do not make use of a vacuum to inflate the gloves, but nevertheless suffer from similar problems as described above. For example, in U.S. Pat. No. 4,228,935, a wrist portion in the form of a relatively rigid toroidal-like member is receivable in a holding rack for enabling the glove to be donned and removed. In U.S. Pat. No. 4,898,309 regular elastic gloves are manually stretched over the open end of a tubular member facilitating entry of the hand into the glove, but at the same time contaminating the glove in the initial glove stretching process.

All the aforementioned prior art devices either require the manual manipulation of a regular-type elastic glove over a stiff lip or ring, increasing the possibility of contamination of the glove, or alternatively require the gloves to come in prepared packages comprising such a ring, resulting in much higher unit costs for the gloves than with regular gloves.

It is therefore an aim of the present invention to provide a system and method which overcomes the aforementioned limitations of glove donning systems and methods.

It is another aim of the present invention to provide a system for facilitating the donning of gloves in a substantially contamination free manner.

It is another aim of the present invention to provide a system for the donning of gloves which enables elasticated gloves such as NRL gloves to be donned relatively easily without the need for lubrication of the gloves.

It is another aim of the present invention to provide such a system in which standard elastic gloves may be donned in a substantially contamination free manner.

It is another aim of the present invention to provide such a system in which each glove can be checked for leakage, and thus for the existence of pinholes therein, prior to donning.

It is another aim of the present invention to provide such a system that is simple to use.

It is another aim of the present invention to provide such a system that is relatively simple mechanically and thus economic to produce as well as to maintain.

The present invention achieves these and other aims by providing a glove donning system in the form of a glove grasping means, typical a vacuum wand, adapted to grasp the outer skin of the cuff portion of a glove, and means are provided to transport the glove into a vacuum chamber such that the cuff portion of the glove is more-or-less aligned with the perimeter or rim of the opening of the vacuum chamber. By grasping only the outer skin of the glove, the cuff portion is gently opened sufficiently to enable an inflatable ring to be inserted into the cuff portion in the deflated state. The ring is then inflated while positioned inside the cuff portion so that the cuff portion is stretched and expanded until it touches the rim of the vacuum chamber. The rim is provided with a suction ring capable of generating sufficient suction to keep the cuff of the glove pressed against the rim, at which point the inflatable ring may be deflated and removed with the grasping means. With the glove thus held within the vacuum chamber, a vacuum is applied to the chamber inflating the glove and thus enabling a hand to be inserted into the glove. A donning device may be fitted with a pair of such systems, one for each hand, and further provided with suitable means for stacking and delivering on demand one glove to each vacuum chamber.

SUMMARY OF INVENTION

The present invention relates to a system for expanding a cuff portion of an elastically expandable glove from a non-expanded condition to an expanded open condition and for releasably holding said cuff portion in said open condition, said open condition being at least sufficient to enable a hand to pass through the cuff portion of the glove, the system comprising:

holding means comprising suction means and at least one suitable contact surface for sealingly holding said cuff portion in said open condition when said cuff portion is in abutting contact with said at least one contact surface: and expandable ring means capable of being reversibly expanded from a first configuration to a second configuration and capable of being contracted from said second configuration to said first configuration, wherein in said first configuration said ring means comprises a compact external profile such as to enable said ring means to be inserted into said cuff portion when said glove is in said non-expanded condition, and wherein in said second configuration said ring means comprises an expanded external profile at least substantially complementary to that of said at least one contact surface to enable the cuff portion to be abutted thereagainst.

Preferably, said holding means are sealing mountable to an open end of a vacuum chamber such that a glove held by said holding means extends into said vacuum chamber, said vacuum chamber being adapted for expanding a portion of said glove extending into said chamber by the application of a vacuum to the external surface of said portion of said glove when said cuff portion is sealing held in said open condition by said holding means.

Optionally, said vacuum means comprises a vacuum chamber operatively connected to a vacuum source and further comprises suction apertures in close proximity to said at least one contact surface for providing suction to at least part of said cuff portion when said cuff portion is in abutting contact with said at least one said contact surface.

Preferably, said at least one contact surface comprises a concave cylindrical surface, and optionally, wherein said holding means comprises first and second axially displaced holding members each having a central aperture comprising at least one said contact surface, wherein said central apertures are substantially coaxially aligned, and wherein said suction apertures are intermediate said at least one contact surface of each said central aperture. Further optionally, said suction apertures are comprised in a suitable mesh, said mesh being axially joined to said first and second holding members.

In a first embodiment, said expandable ring means comprises a substantially toroidal inflatable member capable of being inflated by the application of a pressurised gas at least from said first configuration to said second configuration, and further comprises a pipe in open communication with the interior of the said ring, said pipe being connectable to a suitable pressurised gas source. Preferably, in said first configuration, said ring comprises a substantially flattened transverse profile. Optionally, said ring means further comprises suitable probe means extending downstream of said ring means, said probe in cans having a head comprising at least one nozzle means for directing pressurised gas in a downstream direction, said probe means further comprising a compressed gas line in communication with said probe head, said probe being connectable to a suitable pressurised gas source. Preferably, said head comprises a relatively narrow transverse profile with respect to the transverse profile of said ring means in said first configuration. Typically, said head is insertable in between the substantially flattened opposed surfaces of the said cuff portion when said cuff portion is in a substantially collapsed flattened condition. The probe means is capable of providing compressed gas flow into the glove when at least said head is inserted in-between the substantially flattened opposed surface of the said cuff portion when said cuff portion is in a substantially collapsed flattened condition. The compressed gas flow provided by said head is at least sufficient to separate said opposed flattened surface to enable said ring means in said first configuration comprising a substantially flattened transverse profile to be inserted into said cuff portion.

In the first embodiment, and in said second configuration, said ring comprises a substantially toroidal shape having a transverse diameter at least equal to the internal diameter of said contact surface, and wherein at least a portion of said ring is capable of adopting a profile substantially complementary to said at least one contact surface when in abutting contact therewith directly or indirectly via said cuff portion such as to provide a contact area with said contact surface having a predetermined axial length, typically, between about 10 mm and about 30 mm.

In a second embodiment, said expandable ring means comprises a substantially inflatably stretchable tubular sleeve attached at each end thereof onto a substantially rigid inner member. The sleeve is capable of being inflated by the application of a pressurised gas at least from said first configuration to said second configuration, and further comprises a pipe in open communication with a space between the interior of the said sleeve and the inner member, said pipe being connectable to a suitable pressurised gas source. Optionally, said ring means further comprises suitable probe means extending downstream of said ring means, said probe in cans having a head comprising at least one nozzle means for directing pressurised gas in a downstream direction, said probe means further comprising a compressed gas line in communication with said probe head, said probe being connectable to a suitable pressurised gas source. Preferably, said head comprises a relatively narrow transverse profile with respect to the transverse profile of said ring means in said first configuration. Typically, said head is insertable in between the substantially flattened opposed surfaces of the said cuff portion when said cuff portion is in a substantially collapsed flattened condition. The probe means is capable of providing compressed gas flow into the glove when at least said head is inserted in-between the substantially flattened opposed surface of the said cuff portion when said cuff portion is in a substantially collapsed flattened condition. The compressed gas flow provided by said head is at least sufficient to separate said opposed flattened surface to enable said ring means in said first configuration comprising a substantially flattened transverse profile to he inserted into said cuff portion.

In the second embodiment, and in said second configuration, said sleeve comprises a form similar to an ellipsoid of revolution having a transverse diameter at least equal to the internal diameter of said contact surface, and wherein at least a portion of said sleeve is capable of adopting a profile substantially complementary to said at least one contact surface when in abutting contact therewith directly or indirectly via said cuff portion such as to provide a contact area with said contact surface having a predetermined axial length, typically, between about 10 mm amid about 30 mm.

Optionally, the system of the present invention further comprises cuff-portion inter-surface separation means for separating the substantially flattened opposed surfaces of the said cuff portion when said cuff portion is in a substantially collapsed flattened condition. In the preferred embodiment, said inter-surface separation means comprises a vacuum wand capable of applying suction to a portion of one said flattened opposed surfaces when in close proximity thereto such as to separate this flattened surface from the opposed flattened surface such as to provide an opening in said cuff portion of the glove. Said opening typically comprises a transverse profile sufficiently large to enable said ring means to be inserted into said cuff portion when in said first configuration. The vacuum wand typically comprises at least one suction port and a vacuum line in fluid communication thereto, said vacuum line being connectable to a suitable vacuum source, and the vacuum wand provides a suction force on said one flattened surface sufficient to enable translational and/or rotational motions to be imparted to said glove via said vacuum wand.

In the preferred embodiment, the vacuum wand is mounted onto a first transport means to enable said vacuum wand to he translated and/or rotated within a predetermined working volume. Also, the ring means is mounted onto a second transport means to enable said ring means to be translated and/or rotated within a predetermined working volume. Preferably, the holding means are comprised within said working volume.

The present invention is also directed to a method for expanding a cuff portion of an elastically expandable glove from a non-expanded condition to an expanded open condition and for releasably holding said cuff portion in said open condition, said open condition being at least sufficient to enable a hand to pass through the cuff portion of said glove, comprising the steps of- (a) providing holding means;

(b) providing ring means;

(c) inserting said ring means while in said first configuration into the said cuff portion, said cuff portion being in said non-expanded condition;

(d) expanding said ring means to said second configuration such as to expand said cuff portion onto abutting contact with said contact surface, said holding means being suitably aligned with said ring means;

(e) applying suction to said cuff portion via said suction means such as to maintain said cuff portion in contact with said contact surface;

(f) reducing the external profile of said ring means from said second configuration, and removing said ring means from said cuff portion.

Said method optionally further comprises the following steps:

(g) providing said probe means;

(h) inserting said probe means into said cuff portion, said cuff portion being in said non-expanded condition;

(i) providing compressed air into said glove via said probe means such as to separate opposed flattened surface of said cuff portion to enable said ring means to be inserted into said cuff portion, said ring means being in said first configuration comprising a substantially flattened transverse profile.

wherein steps (g) to (i) are performed between steps (b) and (c).

Further, the method optionally further comprises the following steps:-

(j) providing said inter-surface separation means;

(k) placing said suction port of said vacuum wand in close proximity to the external surface of one opposing flattened surface of said cuff portion, said cuff portion being in said non-expanded condition;

(l) providing suction to a part of said external of said one flattened surface of said cuff portion via said vacuum wand such as to separate opposed flattened surfaces of said cuff portion to enable said ring means to be inserted into said cuff portion, said ring means being in said first configuration comprising a substantially flattened transverse profile.

wherein steps (j) to (l) are performed between steps (b) and (g).

Alternatively, steps (g), (h) and (i) are not performed, and steps (j) to (l) are performed between steps (b) and (c).

Optionally, the method further comprises the steps:-

(m) providing said first transport means;

(n) transporting said vacuum wand to a position superposed over said one flattened surface of said cuff portion between step (j) and step (k);

Optionally, the method further comprises the steps:

(o) grasping said cuff portion by means of said vacuum wand and transporting said glove via said first transport means to a position within said holding means such that said cuff portion is aligned with said at least one contact surface prior to step (c);

(p) expanding said ring means to a third configuration intermediate said first configuration and said second configuration, wherein in said third configuration, said ring is expanded sufficiently so as to engage and partially expand said cuff portion;

(q) reducing suction from said vacuum wand such as to disengage from said cuff portion prior to step (d).

The method may further optionally comprise the steps:-

(r) providing said second transport means;

(s) expanding said ring means to a third configuration intermediate said first configuration and said second configuration, wherein in said third configuration, said ring is expanded sufficiently so as to engage and partially expand said cuff portion;

(t) reducing suction from said vacuum wand such as to disengage from said cuff portion;

(u) grasping said cuff portion by means of said ring means and transporting said glove via said second transport means to a position within said holding means such that said cuff portion is aligned with said at least one contact surface prior to step (c).

Preferably, the holding means are sealingly mounted to an open end of a vacuum chamber such that a glove held by said holding means extends into said vacuum chamber, said vacuum chamber being adapted for expanding a portion of said glove extending into said chamber by the application of a vacuum to the external surface of said portion of said glove when said cuff portion is sealing held in said open condition by said holding means.

Such a method may be adapted for donning right handed gloves and/or left-handed gloves to a user.

The present invention also relates to an apparatus for donning elastically expandable gloves comprising:

(i) at least one vacuum chamber having an open end, said vacuum chamber operatively connected to a suitable vacuum source;

(ii) holding means mounted onto said open end;

(iii) ring means.

Optionally, said apparatus further comprises glove dispensing means for enabling at Least one glove to be engaged by said ring means, and inter-surface separation means.

Preferably, said apparatus comprises two said vacuum chambers, wherein one said vacuum chamber is adapted for donning left-handed gloves, and wherein the other said vacuum chamber is adapted for donning right-handed gloves.

DESCRIPTION OF FIGURES

FIG. 3 illustrates one embodiment of the inter-surface separation means according to the present invention.

FIG. 5 illustrates another embodiment of the ring means of FIG. 4, incorporating probe means.

FIGS. 9a to 9d illustrate the steps of grasping a glove and re-orienting same for insertion into a vacuum chamber, according to a second aspect of the invention.

FIG. 10 illustrates the step of positioning the glove in a vacuum chamber with the inflatable ring in place.

DISCLOSURE OF INVENTION

The present invention is defined by the claims, the contents of which are to be read as included within the disclosure of the specification, and will now be described by way of example with reference to the accompanying Figures.

The present invention relates to a system for placing, holding and maintaining the cuff of an elastic glove in an open position sealingly abutting the rim at the mouth of a vacuum chamber in which the main body of the glove is inserted. Thus, when a vacuum is applied to the chamber the main body of the glove stretches and effectively inflates enabling a wearer's hand to be inserted into the glove with relative ease.

In particular, the present invention relates to a system for expanding a cuff portion of an elastically expandable glove from a non-expanded condition to an expanded open condition and for releasably holding said cuff portion in said open condition, said open condition being at least sufficient to enable a hand to pass through the cuff portion of the glove, the system comprising:- holding means comprising suction means and at least one suitable contact surface for sealingly holding said cuff portion in said open condition when said cuff portion is in abutting contact with said at least one contact surface; and expandable ring means capable of being reversibly expanded from a first configuration to a second configuration (as used here, "reversibly" indicates that the ring means also is capable of being contracted from the second configuration to the first configuration), wherein in said first configuration said ring means comprises a compact external profile such as to enable said ring means to be inserted into said cuff portion when said glove is in said non-expanded condition, and wherein in said second configuration said ring means comprises an expanded external profile at least substantially complementary to that of said at least one contact surface to enable the cuff portion to be abutted thereagainst.

Such a system may be used with virtually any existing glove donning system comprising a vacuum chamber arrangement with few modifications, and is thus readily retrofittable.

Figure 1:
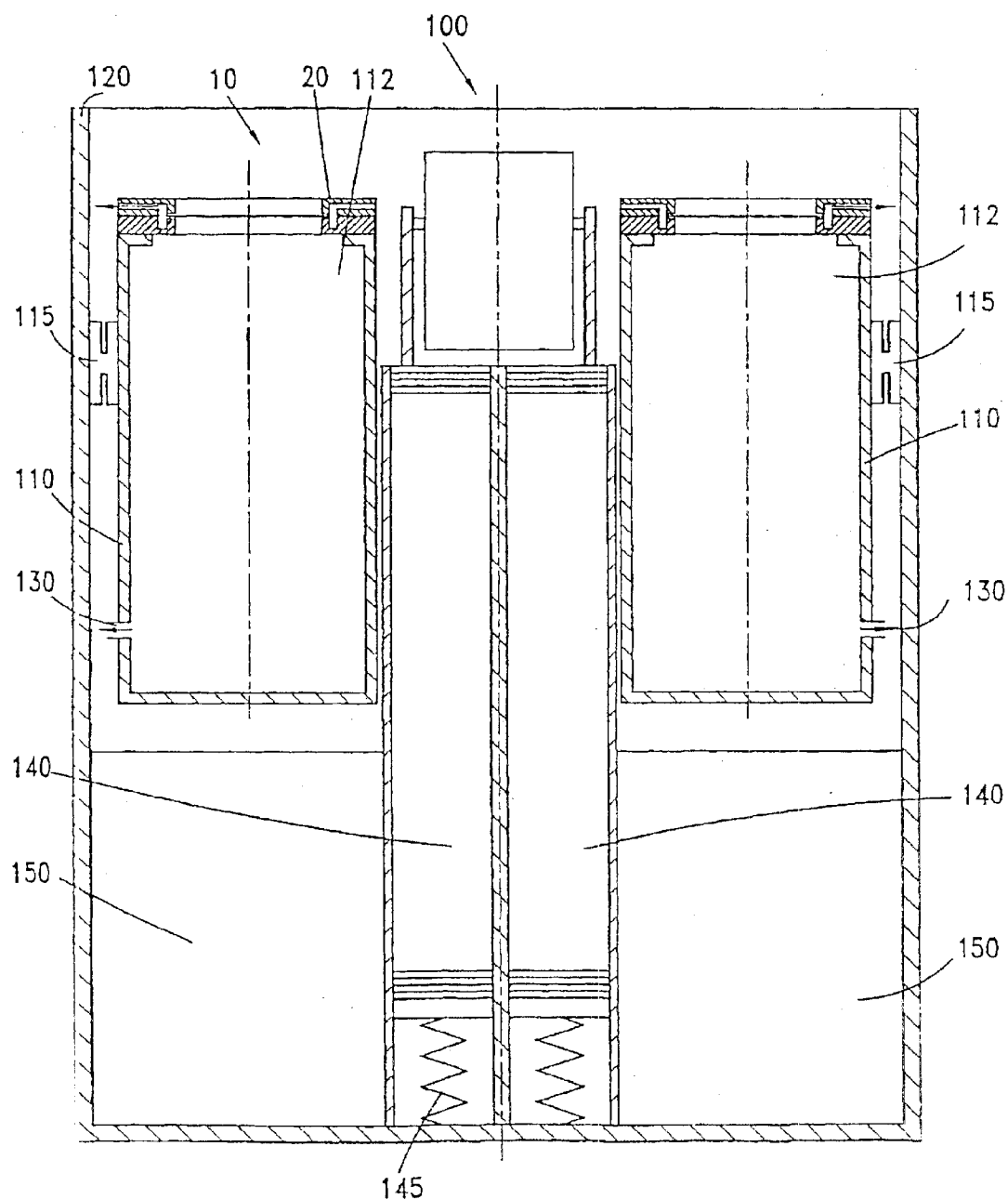
FIG. 1 illustrates the general components of a glove dispensing and donning apparatus incorporating the cuff expansion system of the present invention.

Referring to the figures, FIG. 1 schematically illustrates a cuff expansion apparatus, (100), comprising a pair of cuff expansion systems (10) according to the present invention, one each for enabling the donning of right hand gloves and left hand gloves.

The glove donning apparatus (100) typically further comprises a housing (120) that may be mounted onto a floor or wall, or alternatively onto a trolley or wheeled cart to be easily transportable from one location to another. The housing (120) is open at an upper side thereof, typically including one or a plurality, and typically a pair, of storage chambers (150) for storing sterilised and/or contamination free left-handed and right-handed gloves. The apparatus (100) further comprises a pair of glove magazines (140), one each comprising vertically stacked left-hand or right-hand gloves, and a pair of vacuum chambers (110), one each adapted for the right hand and for the left hand of a user.

Each glove magazine (140) comprises a stacked arrangement of sterilised and/or contamination-free gloves, in which the gloves are all oriented in substantially the same manner, typically in a flattened state with the upper part of the glove (corresponding to the back of the hand) being substantially parallel and in close proximity to the lower part of the glove (corresponding to the palm area). The gloves are elastically expandable, or at least the cuff portions of the gloves are elastically expandable, and are provided in a non-expanded condition. The magazine (140) is adapted for presenting an uppermost glove of a stack of gloves at a particular height within the housing (120), as will be further described hereinbelow, and thus comprises any suitable elevator mechanism (145) to push the stack upwards by a suitable amount whenever the uppermost glove is removed. When the stack of gloves in the magazine (140) is exhausted, a new stack of gloves may be inserted therein from the storage chambers (150) in a contamination free manner.

The vacuum chambers (110) are each supported in the housing (120) in any suitable manner, such as by means of side brackets or preferably by journals (115) which permit the vacuum chambers (110) to be rotated to a horizontal or slanted position to facilitate donning of gloves by a user. Each vacuum chamber (110) is of a generally cylindrical construction and is sized to accommodate the hand of a user including a glove, at least from the tip of the fingers up to the cuff portion and preferably to the middle of the forearm, and the chamber (110) is open at the upper side (112) thereof. Each vacuum chamber (110) comprises a suction pipe (130) for evacuating the chamber, and the suction pipe (130) is connected to a suitable vacuum source such as a suction or vacuum pump or the like (not shown).

Figure 2:
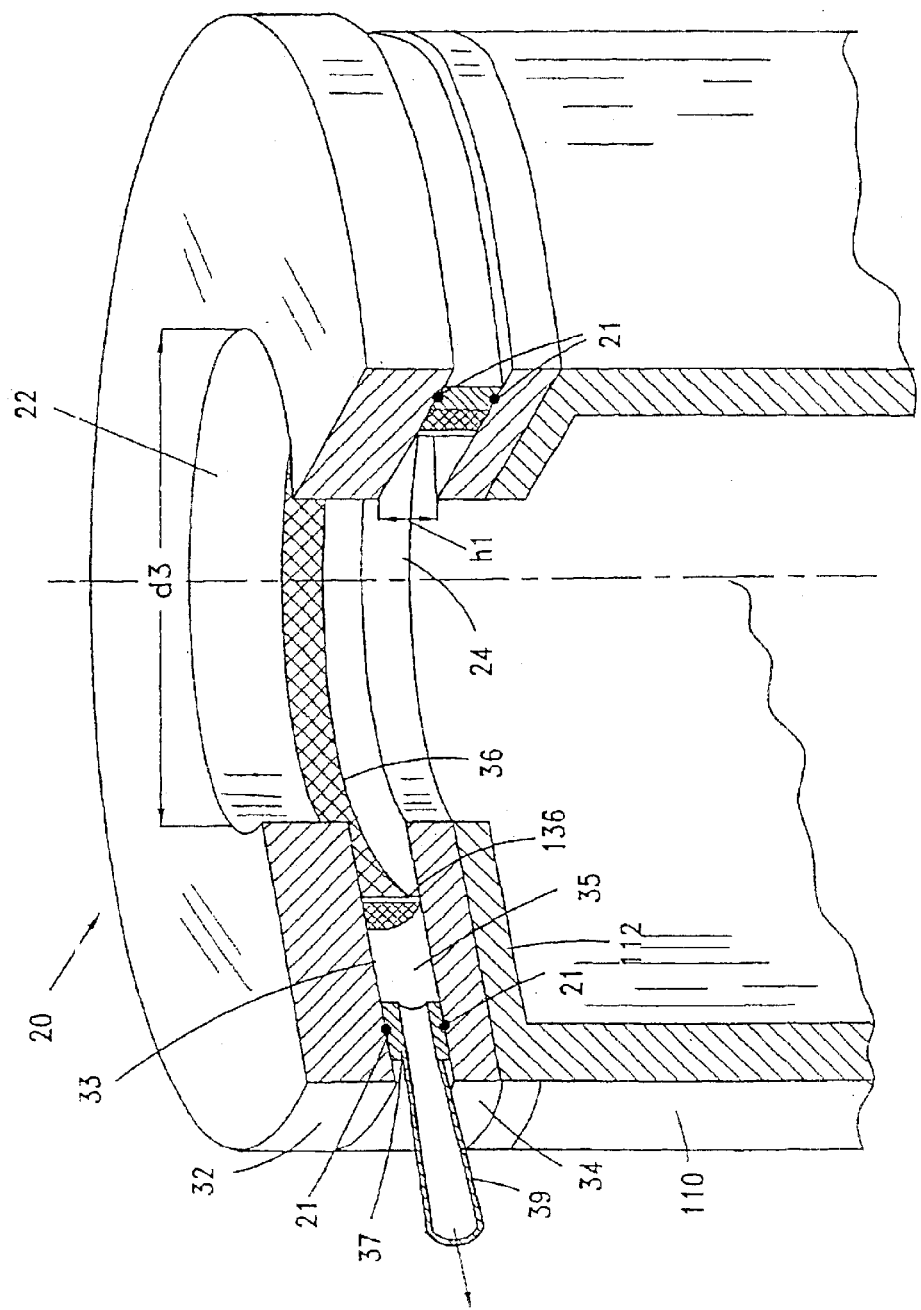
FIG. 2 illustrates in partially sectioned perspective view a holding means according to a preferred embodiment of the present invention.

Referring to FIG. 2, the cuff expansion system (10) of the present invention comprises holding means, which in the preferred embodiment is in the form of a suction ring (20) for each vacuum chamber (110) of said apparatus (100). The suction ring (20) generally comprises first and second preferably coaxial concave cylindrical contact surfaces (22) and (24) adapted for forming a seal with at least portions of the cuff of an elastic glove that has been expanded to abut against the contact surfaces (22) and (24). The said first and said second contact surfaces (22) and (24) are axially separated by suitable suction means (25) adapted to permit suction to be applied between these contact surfaces (22) and (24), and thus retain the cuff portion (200) of the glove sealingly abutted against the said contact surfaces (22) and (24) once the cuff portion (200) is properly positioned in such a manner, as will be described hereinbelow, for example. The said contact surfaces (22) and (24) are typically comprised on respective axially spaced annular coaxial discs (32) and (34). The lower disc (34) is adapted to be sealingly mounted onto the upper open end (112) of a vacuum chamber (110). The vacuum means (25) comprises suitable air inlet means (136), disposed axially intermediate said contact surfaces (22) and (24), and further comprises an outlet conduit (39) connected to a suitable vacuum source (not shown) to provide suction to said air inlet means (136). Typically, the said vacuum means (25) is bounded by facing annular surfaces (33) and (35) of said discs (32) and (34), respectively, and by inner and outer cylindrical walls (36) and (37) axially joined thereto. Seals such as suitable O-rings (21) may be provided for sealing between the inner and outer cylindrical walls (36) and (37), and the discs (32), (34). The inner wall (36) comprises said air inlet means (136), and may constitute or comprise a suitable mesh screen, apertures or slits, for example. Said conduit or vacuum pipe (39) may be comprised on the outer wall (37) and connected to a suitable vacuum source such as a suction or vacuum pump or the like (not shown). Many other alternative constructions for the said suction ring (20) are also possible within the scope of the invention.

The said cuff expansion system (10) further comprises inter-surface separation means (40) adapted for separating the opposed flattened surfaces of a glove and optionally also for grasping a glove, preferably from a stack of gloves in said magazine (140). Said inter-surface separation means (40) may comprise any suitable mechanical grasping means such as a mechanical claw, for example. Referring to FIG. 3, in the preferred embodiment of the present invention said inter-surface separation means (40) comprises a vacuum wand (42) having at least one inlet opening (43) for applying a vacuum to one side of a glove, said vacuum wand being operatively connected to a suitable vacuum source. The said wand (42) has a grasping end (44) comprising a suction surface (46) adapted for providing a reasonable seal with one of the external flattened surface of a glove. A plurality of inlet openings (43) are provided on said surface (46) for applying a vacuum to a flattened surface of a glove. The said surface (46) is preferably concavely arcuate so that when a glove is grasped by said wand (42) by the upper flattened side thereof, say, this side is automatically separated from the lower flattened side of the glove, heretofore in juxtaposed close proximity thereto, providing an initial opening (49) at the cuff portion of the glove. The inter-surface separation means (40) may be carried on a suitable transport means capable of providing the necessary translation and rotational movements within a working volume, and typically comprises a mechanical or robotic arm capable of providing the necessary translations along and/or rotations about one or more axes to enable the inter-surface separation means (40) to grasp a glove and to convey it to the vacuum chambers (110).

Referring to FIGS. 4(a) and 4(b), and FIGS. 6(a) and 6(c), the said cuff expansion system (10) further comprises an expandable ring means (50) for extending the cuff portion (200) of a glove into abutting contact with said contact surfaces (22) and (24) of said suction ring (20). The ring means (50) is characterised in being capable of reversibly expanding from a first configuration to a second configuration. The first configuration is such that the ring means (50) is compact enough to be inserted into the cuff portion (200) when the glove is in the non-expanded condition, and in particular into the opening (49) in the cuff section of the glove arising from the glove being grasped and non-elastically opened by the inter-surface separation means (40). The second configuration is such as to provide a profile substantially complementary to that of said contact surfaces (22) and (24), and to enable the cuff portion (200) to be sealingly abutted against these surfaces. If the contact surfaces (22), (24), are, for example elliptical, then the ring means (50) expands to a substantially elliptical profile complementary thereto. In the preferred embodiment, the contact surfaces (22), (24), are substantially cylindrical, and the ring means (50) expands to a substantially cylindrical external profile complementary thereto. The ring means (50) may comprise a suitable mechanical mechanism for expanding from said first configuration to said second configuration.

Figure 4A:
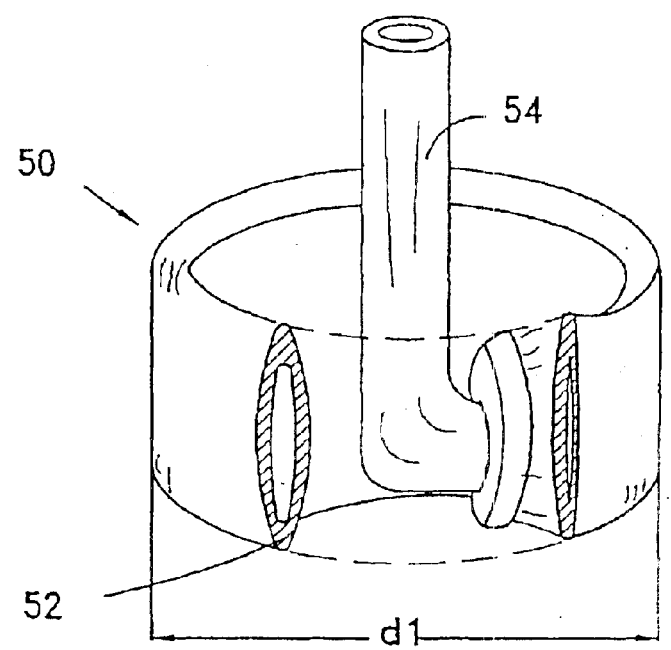
FIGS. 4(a) and 4(b) illustrate in partially sectioned perspective view an embodiment of the expandable ring means of the present invention in the first configuration and the second configuration, respectively.
Figure 4B:
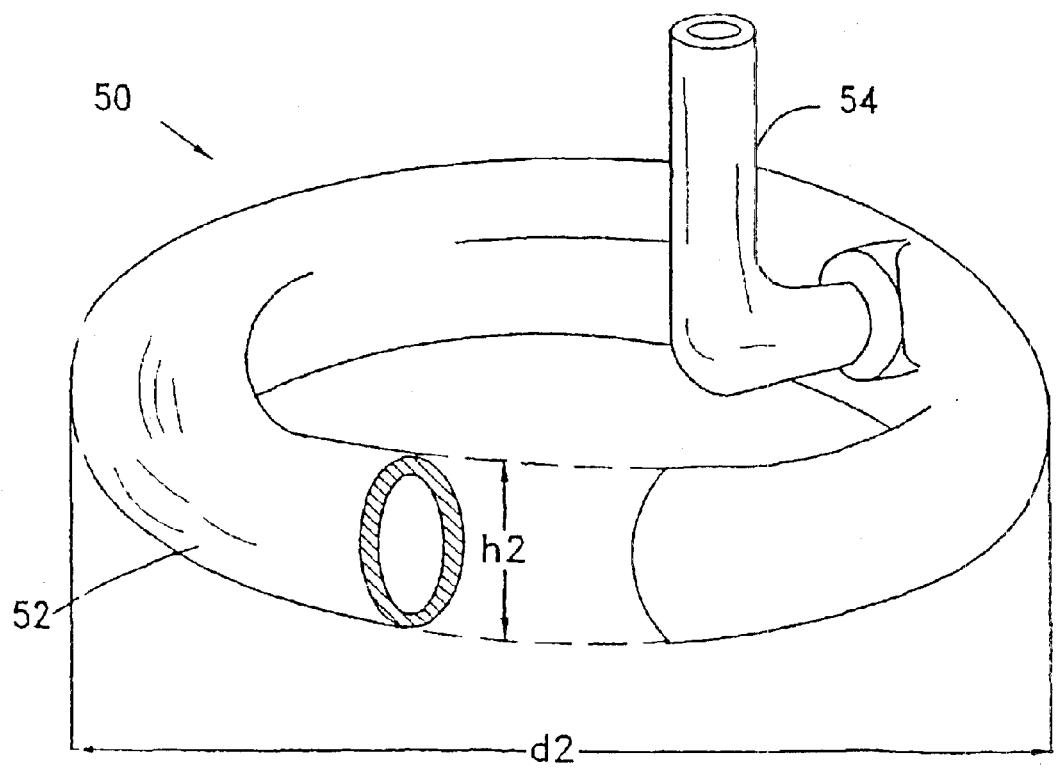

In a first embodiment, referring to FIGS. 4(a) and 4(b), said ring means (50) comprises a substantially toroidal inflatable ring body (52) made from an elastically expandable material capable of being inflated by the application of a pressurised gas, and having gas inlet means (54) for providing pressurised gas, typically air, to the inside of said ring body (52).

Figure 6A:
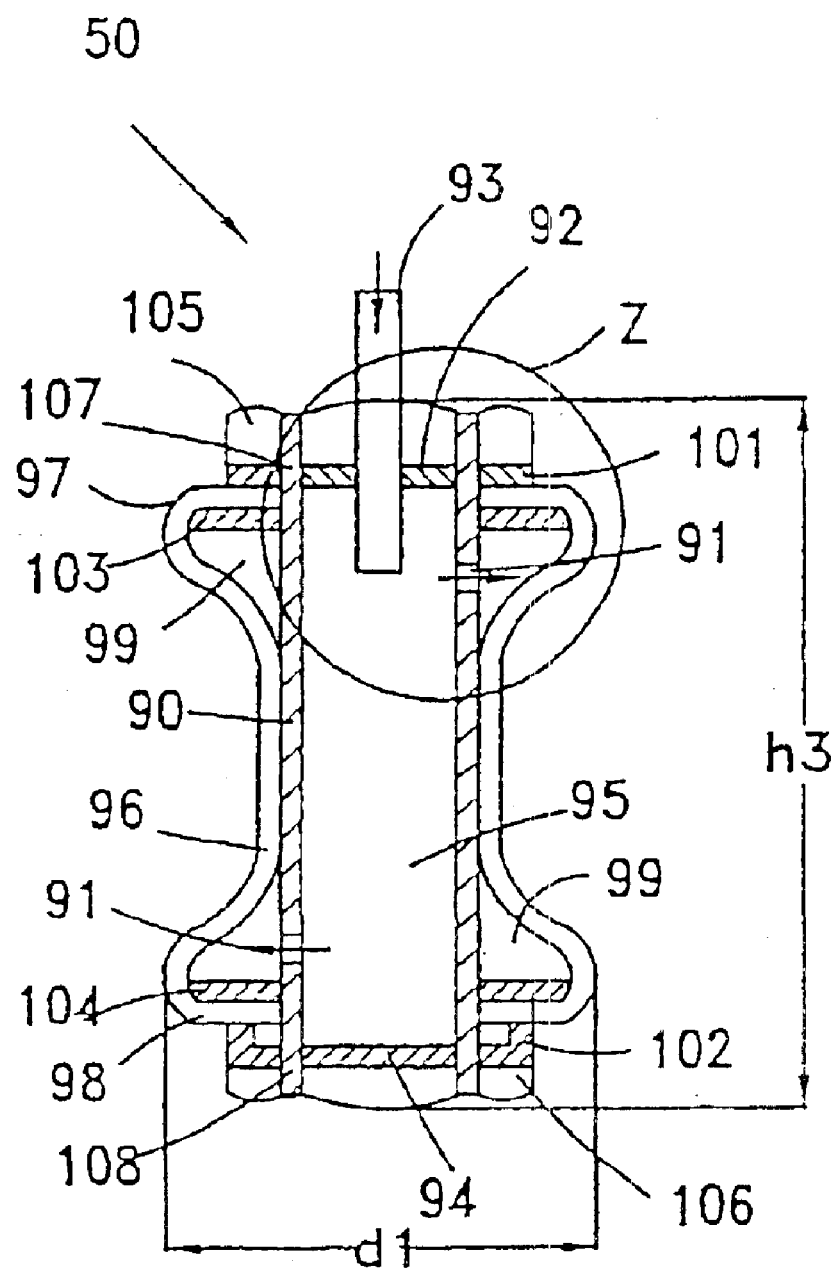
FIGS. 6(a) and 6(c) illustrate in transverse cross-sectional view another embodiment of the expandable ring means of the present invention in the first configuration and the second configuration, respectively.
Figure 6B:
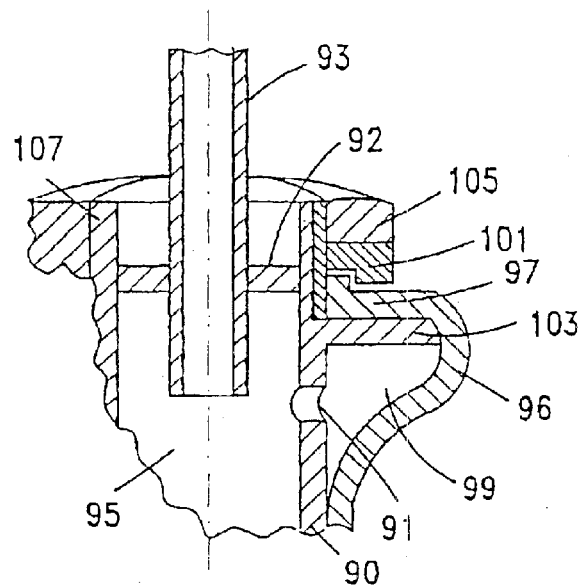
FIG. 6(b) shows detail Z of FIG. 6(a).
Figure 6C:
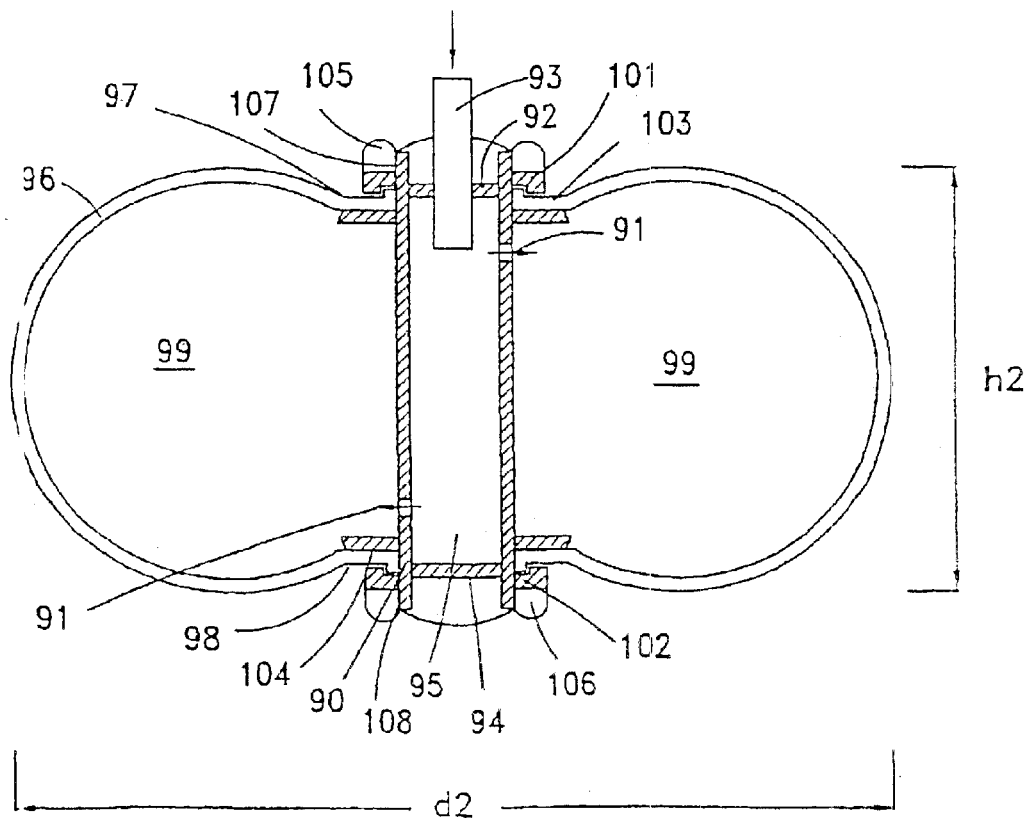

In a second embodiment, and referring to FIGS. 6(a), 6(b) and 6(c), said ring means (50) comprises a substantially rigid inner tubular member (90), one longitudinal end (108) of which is closed by means of wall (94), for example, and the other longitudinal end (107) of which comprises an end wall (92) having a tubing (93) sealingly mounted with respect thereto for providing fluid communication between a pressurised air or gas source (not shown), and the inside (95) of said member (90). An expandably stretchable and flexible tubular sleeve (96) is sealing attached at each longitudinal end (97), (98) thereof to corresponding ends (107), (108) respectively, of the tubular member (90). The sleeve (96) may be sealingly attached to the tubular member (90) by suitable adhesive. Preferably, though, the longitudinal ends (97), (98) of the sleeve (96) are stretched over enlarged rings (103), (104), respectively, and are clamped in place by means of outer rings (101), (102) respectively, which fit tightly over the ends (97), (98) of the sleeve (96) and over the member (90). Nuts (104), (105) screwed onto the ends (107), (108) respectively, of the tubular member (90) press the outer rings (101), (102) towards the inner rings (103), (104), respectively, thereby grippingly pinching the ends of the sleeve (96) in place. Optionally, the inner rings (103), (104) are in the form of radially extending discs to assist the sleeve (96) in assuming the form of an ellipsoid of revolution illustrated in FIG. 6(c). At least one, and preferably a plurality of, apertures (91) provide communication between the inside (95) of the tubular member (90) and the space (99) between the sleeve (96) and the member (90). Pressurised air or gas (not shown), supplied via tube (93), flows to the space (99), thereby inflating the sleeve (96) as illustrated in FIG. 6(c). When air pressure is removed from, or suction applied to, tube (93), the sleeve (96) resumes its datum un-stretched condition, as illustrated in FIG. 6(a). Optionally, nut (106) may replace wall (94) if nut (106) is adapted for sealing the end (108) of tube (90). Similarly, nut (105) may optionally replace wall (92) if nut (105) is adapted for sealing end (107) of tube (90), while providing a suitable aperture for sealingly mounting therein tubing (93).

As illustrated in FIGS. 4(a) and 4(b), and FIGS. 6(a) and 6(c), in the first and second embodiments, said expandable ring means (50) is thus capable of being reversibly expanded from a first configuration having diameter (d1) to a second configuration having diameter (d2), wherein (d2) is substantially greater than (d1), and wherein:

(a) said first diameter (d1) is such as to enable the ring means (50) to be inserted into the cuff portion (200) of a glove via opening (49) arising from the glove being grasped by said grasping means (40); and wherein (b) said second diameter (d2) is at least equal to the diameter (d3) of said contact surfaces (22) and (24).

Furthermore, the height (h2) of the ring means (50), at least when fully expanded or inflated is at least a little greater than the spacing (hi) between said contact surfaces (22) and (24) in order to maintain sealing contact of the cuff portion (200) of the glove with said contact surfaces (22), (24) at least until vacuum is applied to said suction means (25).

Rather than a transverse circular profile, the ring means (50) may alternatively comprise a substantially flattened or elliptical transverse profile which is more readily accommodated within the typically elongated transverse profile of the opening (49).

Typically, and by way of non-limiting example, in the first embodiment of the ring means (50), said ring body (52) may comprise a first diameter (d1) of about 40 mm to about 50 mm, and a height (h2) of about 30 mm and preferably up to about 50 mm, while the internal diameter (d3) of the surfaces (22), (24) may be about 130 mm.

Similarly, and by way of non-limiting example, in the second embodiment of the ring means (50), said tubular member (90) may comprise a first diameter (d1) of about 15 mm to about 20 mm, and a height (h2) of about 50 mm, while the internal diameter (d3) of the surfaces (22), (24) may be about 130 mm.

Figure 7:
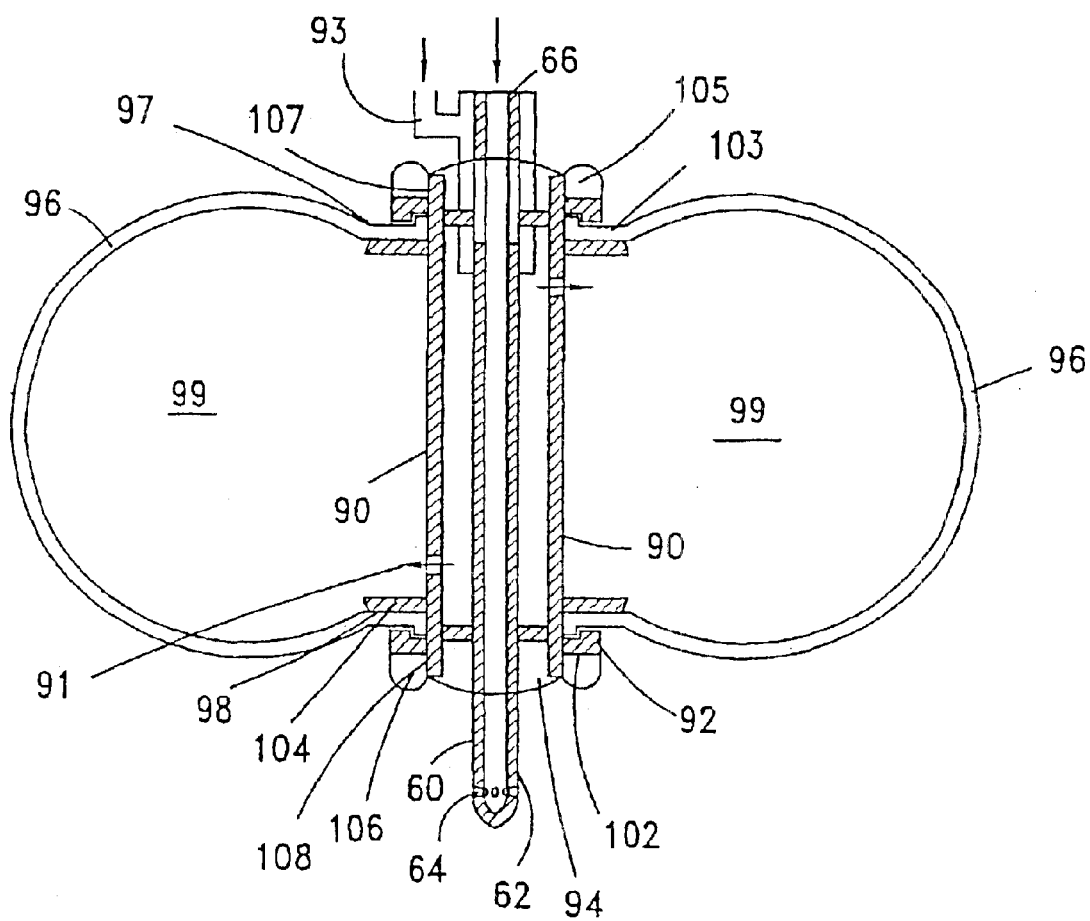
FIG. 7 illustrates another embodiment of the ring means of FIGS. 6(a) to 6(b), incorporating probe means.
Figure 8A:
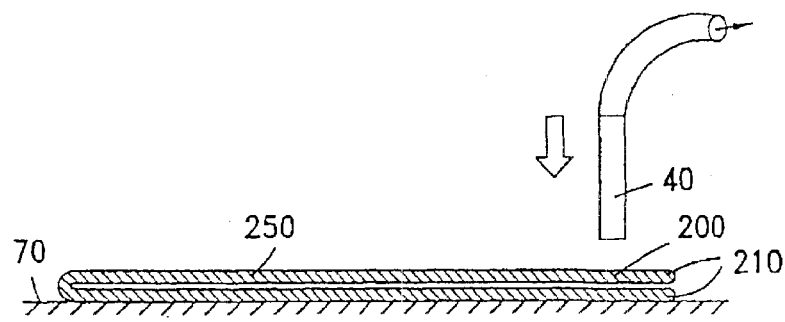
FIGS. 8a to 8d illustrate the steps of grasping a glove and re-orienting same for insertion into a vacuum chamber, according to one aspect of the invention.
Figure 8B:
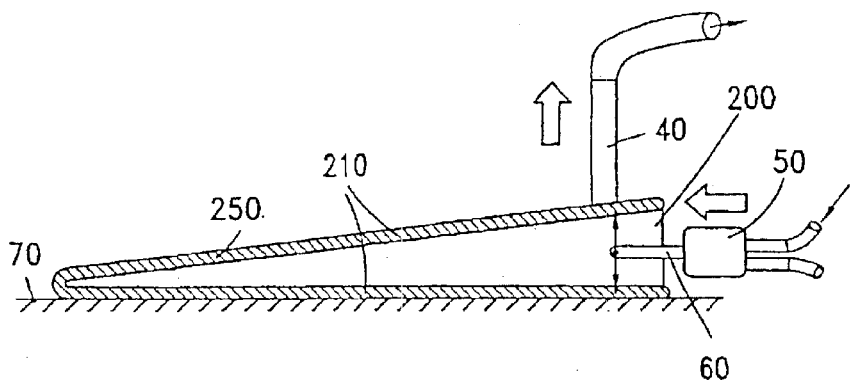
Figure 8C:
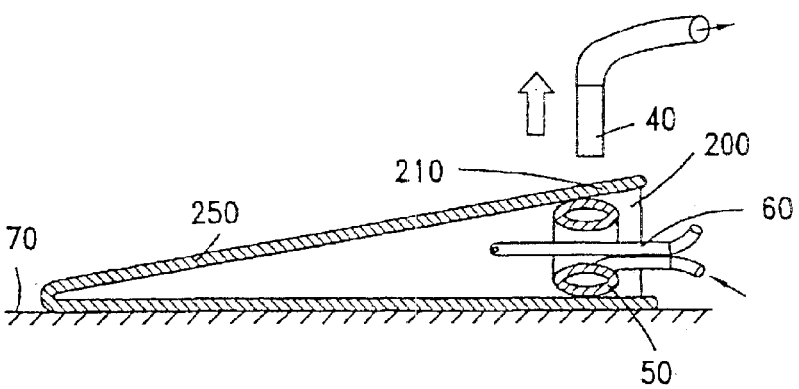
Figure 8D:
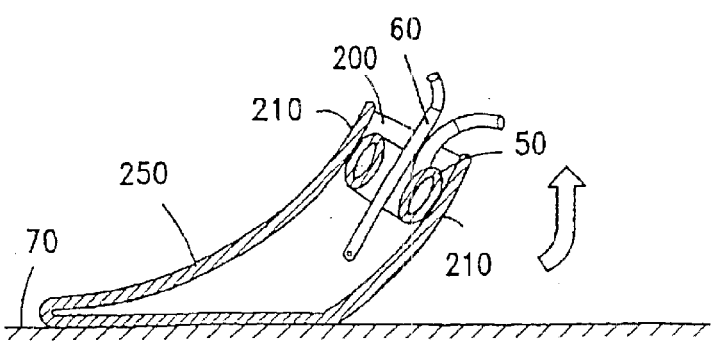
Figure 9A:
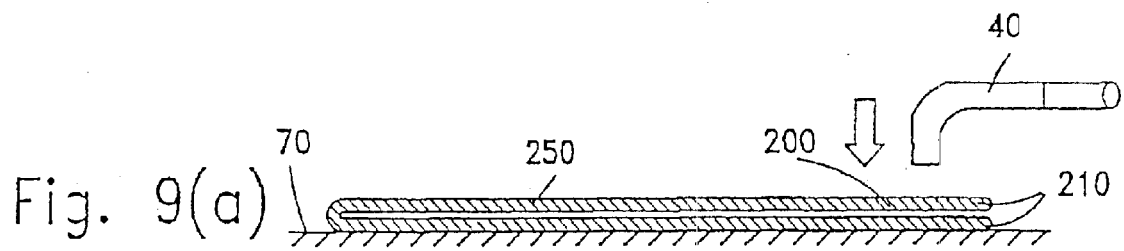
Figure 9B:
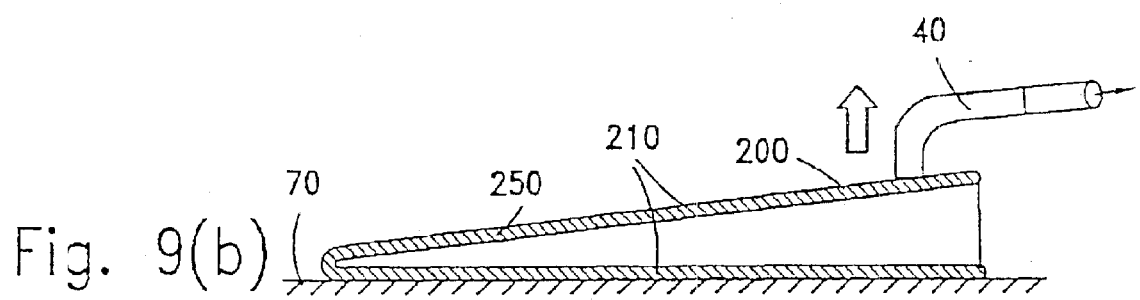
Figure 9C:
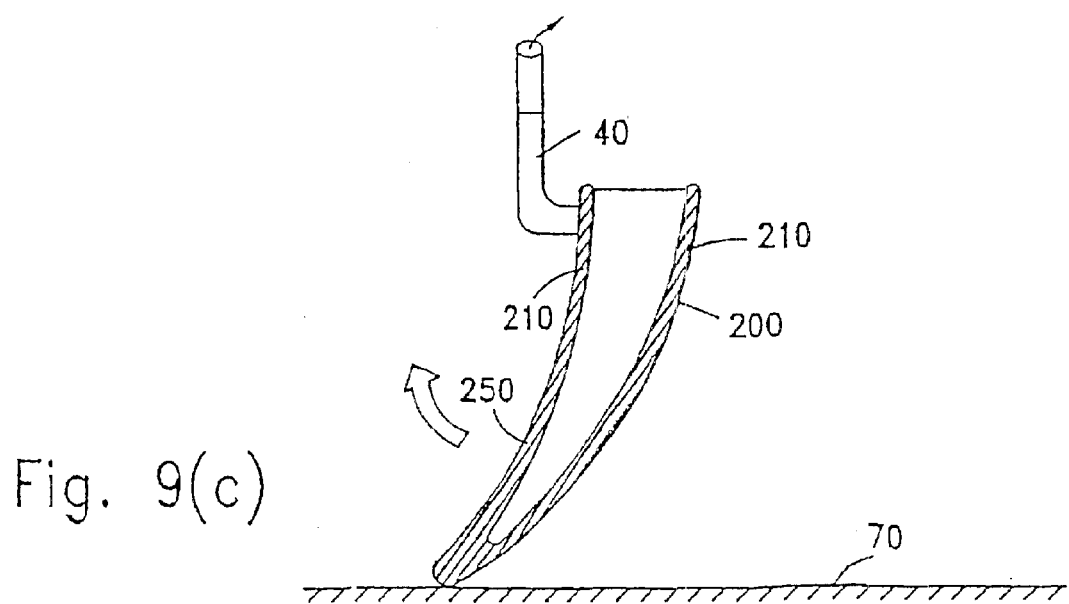

Optionally, and referring to FIGS. 5 and 7 for the first and second embodiments of said ring means (50), respectively, said ring means (50) further comprises suitable probe means (60) extending downstream of said ring means. The probe means (60) has a head (62) comprising at least one nozzle means for directing pressurised gas in a downstream direction. The nozzle means are preferably in the form of a plurality of radial apertures (64). The probe means (60) further comprising a compressed gas line (66) in communication with said probe head (62), said pressurised gas line being connectable to a suitable pressurised gas source (not shown). The probe head (62) preferably comprises a relatively narrow transverse profile with respect to the transverse profile of said ring means (50) when this is in said first configuration. The probe head (62) is adapted to be insertable in-between the substantially flattened opposed surfaces (210) of the said cuff portion (200) when said cuff portion (200) is in a substantially collapsed flattened condition. The said probe means (60) is capable of providing compressed gas flow into the glove (250) when at least said head (62) is inserted in-between the substantially flattened opposed surfaces (210) of the said cuff portion (200) when said cuff portion (200) is in a substantially collapsed flattened condition. The compressed gas flow provided by said head (62) should be at least sufficient to separate said opposed flattened surfaces (210) to enable said ring means (50) in said first configuration, optionally comprising a substantially flattened transverse profile, to be inserted into said cuff portion (200).

The expandable ring means (50) may be carried on a suitable transport means capable of providing the necessary translation and rotational movements within a working volume, and typically comprises a mechanical or robotic arm capable of providing the necessary translations along and/or rotations about one or more axes to enable the ring means (50) to be inserted into the cuff portion (200) of the glove (250) when in the non-expanded condition, typically opening (49) provided by grasping means (40) acting on the cuff portion (200) of a glove (250), and where necessary to the vacuum chambers (110), and particularly to position the ring means (50) in axial alignment with the vacuum means (136) of the suction ring (20).

The present invention also relates to a method for expanding a cuff portion of an elastically expandable glove from a non-expanded condition to an expanded open condition and for releasably holding said cuff portion in said open condition, said open condition being at least sufficient to enable a hand to pass through the cuff portion of said glove.

The system (10) of the present invention may be used as follows. Referring to FIGS. 8(a) to 8(d), in step (a) the inter-surface separating means (40) is brought by suitable transport means into approximate vertical alignment with the cuff portion (200) of a glove (250) that is lying substantially flat on a horizontal surface (70). The horizontal surface (70) may be a platform, though preferably it may be another glove (250) on a vertical stack of gloves of a magazine (140), or indeed the bottom of the magazine (140) itself, this being the last glove therein. In step (b), the grasping means (40) then grasps the cuff portion (200) of the upper side of the glove (250) such as to separate the upper and lower sides (210) of the glove and provide an opening (49) at the cuff portion (200) of the glove (250). Alternatively, though preferably additionally, the probe means is brought into proximity to the opening of the glove (200) and inserted in-between the opposed surfaces (210) of the cuff portion (200), and compressed air is delivered via said apertures (64) into at least the cuff portion (200), separating the opposed surfaces (210). In step (c), the ring means (50), in said first configuration, is inserted into the opening (49) by suitable means and expanded to a third configuration intermediate said first and second configurations. In the third configuration, the ring means (50) is expanded to an extent sufficient to at least slightly expand the cuff portion (200) of the glove (250) and thus grasp and hold the glove (250) from the inside thereof. Such an expansion should be to less than that constituting the said second configuration of the ring means (50), and may be accomplished in the first embodiment by providing suitable pressurised gas, typically air, to the ring body (52) via inlet pipe (54), and in the second embodiment by to the space (99) via pipe (93). The inter-surface separating means (40) may then be removed, in the preferred embodiment by first removing the vacuum provided thereby and then physically distancing the vacuum wand (42) from the glove (250). In step (d), suitable means rotate the ring means (50) together with the glove (250) held therewith such that the glove (250) is oriented substantially vertically, with the cuff portion (250) uppermost. Suitable transport means then transport the glove (250) held by the ring means (50) into vacuum chamber (110) such that the ring means (50) is axially aligned with the suction means (25) of the suction ring (20) thereof, as illustrated in FIG. 10.

FIGS. 9(a) to 9(d) illustrate an alternative though similar procedure to that illustrated in FIGS. 8(a) to 8(d), the main difference being in that in steps (b) and (c), the inter-surface separating means (40) grasps and rotates a glove (250) by suitable transport means such that the glove (250) is oriented substantially vertically, with the cuff portion (200) uppermost. In step (d), suitable transport means transport the glove (250) held by the inter-surface separating means (40) into vacuum chamber (110). Then, in step (d), the ring means (50), in said first configuration, is inserted into the opening (49) by suitable transport means, optionally using said probe means (60) to facilitate the insertion thereof in a similar manner as described above with respect to FIG. 8, mutatis mutandis. Then, the ring means (50) is expanded to said third configuration such as to internally grasp the cuff portion (200). The ring means (50) is thus expanded to an extent sufficient to at least slightly expand the cuff portion (200) of the glove (250) and thus grasp and hold the glove (250) from the inside thereof. As before, such an expansion should be to less than that constituting the said second configuration of the ring means (50), and may be accomplished in the preferred embodiment by providing suitable pressurised gas, typically air, to the ring body (52) via inlet pipe (54) for the first embodiment, or to the space (99) via pipe (93) for the second embodiment. The inter-surface separation means (40) may then be removed, in the preferred embodiment by first removing the vacuum provided thereby and then physically distancing the vacuum wand (42) from the glove (60). The ring means (50) is then axially aligned with the suction means (25) of the suction ring (20) thereof, as illustrated in FIG. 10.

Figure 11:
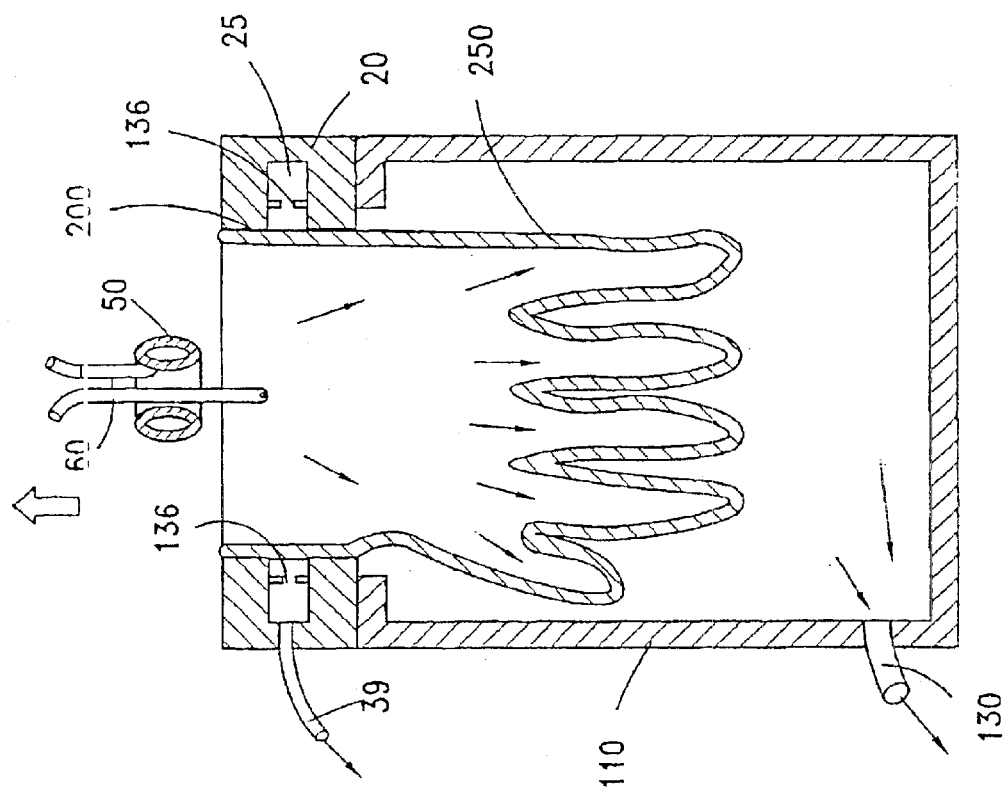
FIG. 11 illustrates the step of inflating the inflatable ring of FIG. 10.
Figure 12:
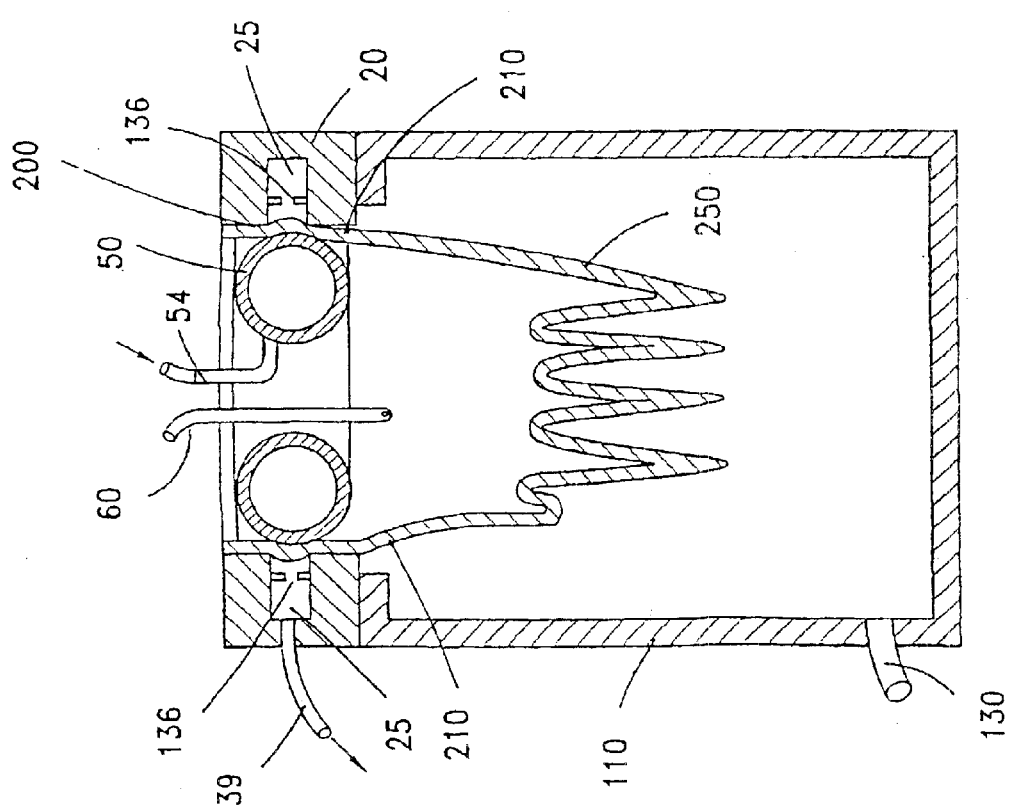
FIG. 12 illustrates the step of deflating and removing the inflatable ring of FIG. 4 after the cuff portion of the glove is grasped in place by the holding means of the vacuum chamber, and the step of evacuating the vacuum chamber to inflate the glove.

Once the glove (250) is held in vertical orientation within the vacuum chamber (110), with the ring means (50) aligned with the inlet opening (136) of said suction means (25) of the suction ring (20), the ring means (50) is expanded to said second configuration, such that the outer surface of the cuff portion (200) of the glove (250) is abutted against the said contact surfaces (22) and (24). In the preferred embodiment this is accomplished by providing pressurised gas, typically air, to the ring body (52) via inlet pipe (54) to inflate the ring body (52) to at least a diameter (d3), as illustrated in FIG. 11 for the first embodiment of the ring means (50). In a similar manner, the sleeve (96) may be inflated via pipe (93) to a similar diameter (d3) for the second embodiment. When sealing contact is established between the outer surface of the cuff portion (200) and the contact surfaces (22), (24), a vacuum applied to the suction ring (20) via suction means (25) causes the cuff portion (200) of the glove to be held onto the suction ring (20). At this point, the ring means (50) may be retracted, or deflated, to a diameter substantially smaller than (d3), and preferably to that corresponding to said first configuration, and suitable transport means remove the said ring means (50) from the glove (250), as illustrated in FIG. 12. A suitable vacuum may now be applied to the vacuum chamber (110) in the usual manner, enabling the glove (250) to expand downstream of the cuff portion (200) under the influence of the higher ambient pressure in the wearer environment, enabling a wearer's hand to be inserted into the glove (250) with relative ease. The relatively large opening to the glove provided by the adherence of the cuff to the suction ring (20), and the expansion of the inner volume of the glove, enable the donning of the glove (250) to be accomplished without the need for the glove to be lubricated. The vacuum chambers (110) may then be tilted by any desired angle about journals (115), typically to a horizontal position, to facilitate alignment with a user's forearm.

Advantageously, suitable pressure sensing means (not shown) may be provided to the chamber (110) to check whether the vacuum is being maintained. If it is found that a higher than normal suction pressure is required to maintain the glove (250) inflated within the chamber (110), this could be indicative of a leak from the body of the glove itself, for example due to the presence of pinholes. Thus, by monitoring the pressure in the vacuum chamber (110), it may be determined whether or not each and every glove (250) has potentially dangerous leaks, thus providing an important safety feature.

While FIGS. 8 to 12 illustrate the above described method with respect to the first embodiment of the ring means (50), the method is illustratively similar for the second embodiment of the ring means (50), mutatis mutandis.

While in the foregoing description describes in detail only a few specific embodiments of the invention, it will be understood by those skilled in the art that the invention is not limited thereto and that other variations in form and details may be possible without departing from the scope and spirit of the invention herein disclosed.

What is claimed:

1. A system for expanding a cuff portion of an elastically expandable glove from a non-expanded condition to an expanded open condition and for releasably holding said cuff portion in said open condition, said open condition being at least sufficient to enable a hand to pass through the cuff portion of the glove, the system comprising:
   (a) holding means comprising suction means and at least one suitable contact surface for sealingly holding said cuff portion in said open condition when said cuff portion is in abutting contact with said at least one contact surface; and
   (b) expandable ring means capable of being expanded from a first configuration to a second configuration and capable of being contracted from said second configuration to said first configuration, wherein in said first configuration said ring means comprises a compact external profile such as to enable said ring means to be inserted into said cuff portion when said glove is in said non-expanded condition, and wherein in said second configuration said ring means comprises an expanded external profile at least substantially complementary to that of said at least one contact surface to enable the cuff portion to be abutted thereagainst.

2. A system for expanding a cuff portion as claimed in claim 1, wherein said holding means are sealingly mountable to an open end of a vacuum chamber such that a glove held by said holding means extends into said vacuum chamber, said vacuum chamber being adapted for expanding a portion of said glove extending into said chamber by the application of a vacuum to the external surface of said portion of said glove when said cuff portion is sealing held in said open condition by said holding means.

3. A system for expanding a cuff portion as claimed in claim 1, wherein said suction means comprises a vacuum chamber operatively connected to a vacuum source and further comprises suction apertures in close proximity to said at least one contact surface for providing suction to at least part of said cuff portion when said cuff portion is in abutting contact with said at least one said contact surface.

4. A system for expanding a cuff portion as claimed in claim 3, wherein said at least one contact surface comprises a concave cylindrical surface.

5. A system for expanding a cuff portion as claimed in claim 3, wherein said holding means comprises first and second axially displaced holding members each having a central aperture comprising at least one said contact surface, wherein said central apertures are substantially coaxially aligned, and wherein said suction apertures are intermediate said at least one contact surface of each said central aperture.

6. A system for expanding a cuff portion as claimed in claim 3, wherein said suction apertures are comprised in a suitable mesh, said mesh being axially joined to said first and second holding members.

7. A system for expanding a cuff portion as claimed in claim 4, wherein said expandable ring means comprises a substantially toroidal inflatable member capable of being inflated by the application of a pressurised gas at least from said first configuration to said second configuration, and further comprises a pipe in open communication with the interior of the said ring, said pipe being connectable to a suitable pressurised gas source.

8. A system for expanding a cuff portion as claimed in claim 7, wherein in said first configuration, said ring comprises a substantially flattened transverse profile.

9. A system for expanding a cuff portion as claimed in claim 4, wherein said expandable ring means comprises a substantially inflatably stretchable tubular sleeve attached at each longitudinal end thereof over a substantially rigid inner member, said sleeve capable of being inflated by the application of a pressurised gas at least from said first configuration to said second configuration, and further comprises a pipe in open communication with a space between the interior of the said sleeve and said inner member, said pipe being connectable to a suitable pressurised gas source.

10. A system for expanding a cuff portion as claimed in claim 9, wherein said ring means further comprises suitable probe means extending downstream of said ring means, said probe means having a head comprising at least one nozzle means for directing pressurised gas in a downstream direction, said probe means further comprising a compressed gas line in communication with said probe head, said probe being connectable to a suitable pressurised gas source.

11. A system for expanding a cuff portion as claimed in claim 10, wherein said head comprises a relatively narrow transverse profile with respect to the transverse profile of said ring means in said first configuration.

12. A system for expanding a cuff portion as claimed in claim 11, wherein said head is insertable in-between the substantially flattened opposed surfaces of the said cuff portion when said cuff portion is in a substantially collapsed flattened condition.

13. A system for expanding a cuff portion as claimed in claim 12, wherein said probe means is capable of providing compressed gas flow into the glove when at least said head is inserted in-between the substantially flattened opposed surfaces of the said cuff portion when said cuff portion is in a substantially collapsed flattened condition.

14. A system for expanding a cuff portion as claimed in claim 13, wherein said compressed gas flow provided by said head is at least sufficient to separate said opposed flattened surfaces to enable said ring means in said first configuration comprising a substantially flattened transverse profile to be inserted into said cuff portion.

15. A system for expanding a cuff portion as claimed in claim 7, wherein in said second configuration, said ring comprises a substantially toroidal shape having a transverse diameter at least equal to the internal diameter of said contact surface, and wherein at least a portion of said ring is capable of adopting a profile substantially complementary to said at least one contact surface when in abutting contact therewith directly or indirectly via said cuff portion such as to provide a contact area with said contact surface having a predetermined axial length.

16. A system for expanding a cuff portion as claimed in claim 15, wherein said predetermined axial length is between about 10 mm and about 30 mm.

17. A system for expanding a cuff portion as claimed in claim 1, further comprising cuff-portion inter-surface separation means for separating the substantially flattened opposed surfaces of the said cuff portion when said cuff portion is in a substantially collapsed flattened condition.

18. A system for expanding a cuff portion as claimed in claim 17, wherein said inter-surface separation means comprises a vacuum wand capable of applying suction to a portion of one said flattened opposed surfaces when in close proximity thereto such as to separate this flattened surface from the opposed flattened surface such as to provide an opening in said cuff portion of the glove.

19. A system for expanding a cuff portion as claimed in claim 18, wherein said opening comprises a transverse profile sufficiently large to enable said ring means to be inserted into said cuff portion when in said first configuration.

20. A system for expanding a cuff portion as claimed in claim 18, wherein said vacuum wand comprises at least one suction port and a vacuum line in fluid communication thereto, said vacuum line being connectable to a suitable vacuum source.

21. A system for expanding a cuff portion as claimed in claim 18, wherein said vacuum wand provides a suction force on said one flattened surface sufficient to enable translational and/or rotational motions to be imparted to said glove via said vacuum wand.

22. A system for expanding a cuff portion as claimed in claim 21, wherein said vacuum wand is mounted onto a first transport means to enable said vacuum wand to be translated and/or rotated within a predetermined working volume.

23. A system for expanding a cuff portion as claimed in claim 22, wherein said ring means is mounted onto a second transport means to enable said ring means to be translated and/or rotated within a predetermined working volume.

24. A system for expanding a cuff portion as claimed in claim 22, wherein said holding means are comprised within said working volume.

25. A method for expanding a cuff portion of an elastically expandable glove from a non-expanded condition to an expanded open condition and for releasably holding said cuff portion in said open condition, said open condition being at least sufficient to enable a hand to pass through the cuff portion of said glove, comprising the steps of:
   (a) providing holding means comprising suction means and at least one suitable contact surface for sealingly holding said cuff portion in said open condition when said cuff portion is in abutting contact with said at least one contact surface;
   (b) providing ring means capable of being expanded from a first configuration to a second configuration and capable of being contracted from said second configuration to said first configuration, wherein in said first configuration said ring means comprises a compact external profile such as to enable said ring means to be inserted into said cuff portion when said glove is in said non-expanded condition, and wherein in said second configuration said ring means comprises an expanded external profile at least substantially complementary to that of said at least one contact surface to enable the cuff portion to be abutted thereagainst;
   (c) inserting said ring means while in said first configuration into the said cuff portion, said cuff portion being in said non-expanded condition;
   (d) expanding said ring means to said second configuration such as to expand said cuff portion onto abutting contact with said contact surface, said holding means being suitably aligned with said ring means;
   (e) applying suction to said cuff portion via said suction means such as to maintain said cuff portion in contact with said contact surface;
   (f) reducing the external profile of said ring means from said second configuration, and removing said ring means from said cuff portion.

26. A method for expanding a cuff portion as claimed in claim 25, further comprising the steps of:
   (g) providing probe means extending downstream of said ring means, said probe means having a head comprising at least one nozzle means for directing pressurised gas in a downstream direction, said probe means further comprising a compressed gas line in communication with said probe head, said probe being connectable to a suitable pressurised gas source;

(h) inserting said probe means into said cuff portion, said cuff portion being in said non-expanded condition;

(i) providing compressed air into said glove via said probe means such as to separate opposed flattened surfaces of said cuff portion to enable said ring means to be inserted into said cuff portion, said ring means being in said first configuration comprising a substantially flattened transverse profile, wherein steps (h) and (i) are performed between steps (b) and (c).

27. A method for expanding a cuff portion as claimed in claim 25, further comprising the steps of:

(j) providing said inter-surface separation means for separating the substantially flattened opposed surfaces of the said cuff portion when said cuff portion is in a substantially collapsed flattened condition;

(k) placing said suction port of said vacuum wand in close proximity to the external surface of one opposing flattened surface of said cuff portion, said cuff portion being in said non-expanded condition;

(l) providing suction to a part of said external of said one flattened surface of said cuff portion via said vacuum wand such as to separate opposed flattened surfaces of said cuff portion to enable said ring means to be inserted into said cuff portion, said ring means being in said first configuration, wherein steps (j) to (l) are performed between steps (b) and (c).

28. A method for expanding a cuff portion as claimed in claim 26, further comprising the steps of:

(j) providing said inter-surface separation means for separating the substantially flattened opposed surfaces of the said cuff portion when said cuff portion is in a substantially collapsed flattened condition;

(k) placing said suction port of said vacuum wand in close proximity to the external surface of one opposing flattened surface of said cuff portion, said cuff portion being in said non-expanded condition;

(l) providing suction to a part of said external of said one flattened surface of said cuff portion via said vacuum wand such as to separate opposed flattened surfaces of said cuff portion to enable said ring means to be inserted into said cuff portion, said ring means being in said first configuration, wherein steps (j) to (l) are performed between steps (b) and (g).

29. A method for expanding a cuff portion as claimed in claim 28, further comprising the steps of:

(m) providing said first transport means to enable a vacuum wand mounted thereon to be translated and/or rotated within a predetermined working volume; and (n) transporting said vacuum wand to a position superposed over said one flattened surface of said cuff portion between step (j) and step (k).

30. A method for expanding a cuff portion as claimed in claim 29, further comprising the steps of:

(o) grasping said cuff portion by means of said vacuum wand and transporting said glove via said first transport means to a position within said holding means such that said cuff portion is aligned with said at least one contact surface prior to step (c);

(p) expanding said ring means to a third configuration intermediate said first configuration and said second configuration, wherein in said third configuration, said ring is expanded sufficiently so as to engage and partially expand said cuff portion;

(q) reducing suction from said vacuum wand such as to disengage from said cuff portion prior to step (d).

31. A method for expanding a cuff portion as claimed in claim 29, further comprising the steps of:

(r) providing said second transport means to enable said ring means mounted thereon to be translated and/or rotated within a predetermined working volume;

(s) expanding said ring means to a third configuration intermediate said first configuration and said second configuration, wherein in said third configuration, said ring is expanded sufficiently so as to engage and partially expand said cuff portion;

(t) reducing suction from said vacuum wand such as to disengage from said cuff portion;

(u) grasping said cuff portion by means of said ring means and transporting said glove via said second transport means to a position within said holding means such that said cuff portion is aligned with said at least one contact surface prior to step (c).

32. A method for expanding a cuff portion as claimed in claim 25, wherein said holding means are sealingly mounted to an open end of a vacuum chamber such that a glove held by said holding means extends into said vacuum chamber, said vacuum chamber being adapted for expanding a portion of said glove extending into said chamber by the application of a vacuum to the external surface of said portion of said glove when said cuff portion is sealing held in said open condition by said holding means.

33. A method for expanding a cuff portion as claimed in claim 32 adapted for donning right handed gloves to a user.

34. A method for expanding a cuff portion as claimed in claim 32 adapted for donning left handed gloves to a user.

35. Apparatus for donning elastically expandable gloves comprising:

(i) at least one vacuum chamber having an open end, said vacuum chamber operatively connected to a suitable vacuum source;

(ii) a holding means comprising suction means and at least one suitable contact surface for sealingly holding said cuff portion in said open condition when said cuff portion is in abutting contact with said at least one contact surface; and (iii) ring means capable of being expanded from a first configuration to a second configuration and capable of being contracted from said second configuration to said first configuration, wherein in said first configuration said ring means comprises a compact external profile such as to enable said ring means to be inserted into said cuff portion when said glove is in said non-expanded condition, and wherein in said second configuration said ring means comprises an expanded external profile at least substantially complementary to that of said at least one contact surface to enable the cuff portion to be abutted thereagainst.

36. Apparatus as claimed in claim 35, further comprising glove dispensing means for enabling at least one glove to be engaged by said ring means.

37. Apparatus as claimed in claim 35, further comprising inter-surface separation means for separating the substantially flattened opposed surfaces of the said cuff portion when said cuff portion is in a substantially collapsed flattened condition.

38. Apparatus as claimed in claim 35, comprising two said vacuum chambers, wherein one said vacuum chamber is adapted for donning left-handed gloves, and wherein the other said vacuum chamber is adapted for donning right-handed gloves.

39. Apparatus as claimed in claim 35, further comprising a suitable first pressure sensing means operatively connected to said at least one vacuum chamber for sensing air leakage between a said glove and said vacuum chamber, when a said cuff of said glove is held against said holding means when said apparatus is in operation.

* * * * *